US007411108B2

United States Patent
Elomari et al.

(10) Patent No.: US 7,411,108 B2
(45) Date of Patent: *Aug. 12, 2008

(54) PROCESS FOR THE REMOVAL OF CONJUGATED OLEFINS FROM A MONOOLEFIN STREAM

(75) Inventors: Saleh A. Elomari, Fairfield, CA (US); Richard N. Reynolds, Jr., Point Richmond, CA (US); Steven J. Herron, Kingwood, TX (US); Eduardo J. Baralt, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 659 days.

This patent is subject to a terminal disclaimer.

(21) Appl. No.: 10/823,186

(22) Filed: Apr. 12, 2004

(65) Prior Publication Data

US 2004/0260137 A1 Dec. 23, 2004

Related U.S. Application Data

(63) Continuation-in-part of application No. 09/892,177, filed on Jun. 26, 2001, now Pat. No. 6,720,468.

(60) Provisional application No. 60/215,583, filed on Jun. 30, 2000.

(51) Int. Cl.
C07C 2/02 (2006.01)
C07C 7/144 (2006.01)

(52) U.S. Cl. ........................ 585/818; 585/833; 585/533; 585/311

(58) Field of Classification Search ................. 208/818, 208/833, 533, 311
See application file for complete search history.

(56) References Cited

U.S. PATENT DOCUMENTS 3,043,891 A * 7/1962 Stuckey ...................... 585/818
3,773,844 A * 11/1973 Louis et al. .................. 585/818
5,062,866 A * 11/1991 Ho .................................. 95/50
5,220,091 A * 6/1993 Brinkmeyer et al. ......... 585/660
5,300,126 A 4/1994 Brown et al.
6,132,600 A * 10/2000 Marchesseault et al. ..... 210/143
6,175,050 B1 1/2001 Slaugh et al.
6,184,431 B1 2/2001 Slaugh et al.
6,309,997 B1 10/2001 Fujita et al.
6,720,468 B2 4/2004 Elomari et al.
6,770,723 B2 8/2004 Fujita et al.

FOREIGN PATENT DOCUMENTS

JP 2000355555 A2 12/2000
JP 2001348345 A2 12/2001

* cited by examiner

Primary Examiner—Tam M Nguyen
(74) Attorney, Agent, or Firm—Conley Rose, P.C.; Rodney B. Carroll

(57) ABSTRACT

A method for removing conjugated olefins from a composition comprising contacting the composition with a Diels-Alder dienophile to convert conjugated olefins to a Diels-Alder adduct and arresting the Diels-Alder adduct. A method comprising confining a Diels-Alder dienophile to a first side of a selectively permeable barrier wherein the barrier is more permeable to conjugated olefins and less permeable to Diels-Alder dienophile and Diels-Alder adduct, and contacting a composition comprising mono-olefins and conjugated olefins with the Diels-Alder dienophile to form Diels-Alder adduct, wherein the contacting reduces the concentration of conjugated olefins in the composition. A method for removing conjugated olefins from a composition comprising bubbling the composition through a liquid comprising Diels-Alder dienophile to form a liquid comprising Diels-Alder adduct. A method for removing conjugated olefins from a non-solid composition comprising contacting the composition with a solid comprising Diels-Alder dienophile to form a solid comprising Diels-Alder adduct.

33 Claims, 6 Drawing Sheets

REACTION ASSEMBLY 1 FOR BUTADIENE REMOVAL FROM 1-BUTENE

REACTION ASSEMBLY 2 FOR BUTADIENE REMOVAL FROM 1-BUTENE STREAM

PROCESS FOR THE REMOVAL OF CONJUGATED OLEFINS FROM A MONOOLEFIN STREAM

CROSS-REFERENCE TO RELATED APPLICATIONS

This application is a continuation-in-part of application Ser. No. 09/892,177, filed Jun. 26, 2001 now U.S. Pat. No. 6,720,468 issued Apr. 13, 2004 and entitled "Process for the Removal of Conjugated Olefins From a Monolefin Stream," which claims the benefit of U.S. provisional application Ser. No. 60/215,583, filed on Jun. 30, 2000, each of which is hereby incorporated by reference herein in its entirety.

BACKGROUND OF THE INVENTION

The invention relates to a process for the removal of conjugated olefins from a monoolefin stream such as a stream containing normal alpha olefins.

Monoolefins such as normal alpha olefins can be obtained from streams that have been subjected to, for example, dehydrogenation, cracking, or ethylene oligomerization. Depending upon the production method, the normal alpha olefin stream can contain varying amounts of conjugated olefins. If present in large amounts, the conjugated olefins may be separated from the monoolefins for sale or other use. Methods useful for such a separation include distillation, selective adsorption, selective hydrogenation of the conjugated olefin, dimerization of the conjugated olefin, or complexation of the conjugated olefin.

However, it is very difficult to reduce the conjugated olefins content in a normal alpha olefin stream to low levels by means such as distillation because some isomers have very close boiling points and may form azeotropes with one another preventing complete separation. It is particularly difficult to reduce the levels of conjugated olefins in monoolefin streams below a few hundred parts per million (ppm) by the methods mentioned above. Conjugated olefins can be very undesirable impurities in monoolefins such as normal alpha olefins even in very low concentrations such as a few hundred ppm. Normal alpha olefins (NAOs) are used for applications such as polymerization of monomers to form polyolefins. Examples include polymerization of ethylene to form polyethylene and polymerization of propylene to form polypropylene. Normal alpha olefins such as 1-butene, 1-hexene, and 1-octene, are used in the polyethylene process to provide branching of the resultant polymer. Any conjugated olefin present in a stream containing normal alpha olefins can have a very undesirable impact on the production of polyolefins through catalyst deactivation thus reducing catalyst productivity or by causingcrosslinking of the polymer.

As mentioned above, one method currently used to remove conjugated olefins from olefin streams is by selective hydrogenation. Conjugated olefins can be selectively hydrogenated under the proper conditions and using an appropriate catalyst. Selective hydrogenation allows one to greatly reduce the levels of conjugated olefins in the olefin stream. One commercial process that uses selective hydrogenation is UOP's DeFine process. Selective hydrogenation has the disadvantage in that it is difficult to selectively hydrogenate all of the conjugated olefin without hydrogenating significant amounts of monoolefin or isomerizing a normal alpha olefin to an internal olefin. On the other hand, if one minimizes hydrogenation of the monoolefins significant amounts of conjugated olefins are left unconverted.

Dimerization of the conjugated olefin is also a possible way to remove such conjugated olefin from a monoolefin stream. However, this method does not reduce the conjugated olefin content to very low levels.

For the reasons discussed above, it would be very desirable to have an efficient and economical separation/purification process for the removal of even very low levels of conjugated olefins from a monoolefin stream. The present invention provides such a process.

SUMMARY OF THE INVENTION

Disclosed herein is a method for removing conjugated olefins from a composition comprising: contacting the composition with a Diels-Alder dienophile to convert conjugated olefins to a Diels-Alder adduct; and arresting the Diels-Alder adduct.

Further disclosed herein is a method comprising: confining a Diels-Alder dienophile to a first side of a selectively permeable barrier wherein the barrier is more permeable to conjugated olefins and less permeable to Diels-Alder dienophile and Diels-Alder adduct; and contacting a composition comprising mono-olefins and conjugated olefins with the Diels-Alder dienophile to form Diels-Alder adduct; wherein the contacting reduces the concentration of conjugated olefins in the composition.

Further disclosed herein is a method for removing conjugated olefins from a composition comprising bubbling the composition through a liquid comprising Diels-Alder dienophile to form a liquid comprising Diels-Alder adduct.

Further disclosed herein is a method for removing conjugated olefins from a non-solid composition comprising contacting the composition with a solid comprising Diels-Alder dienophile to form a solid comprising Diels-Alder adduct.

Figure 1:
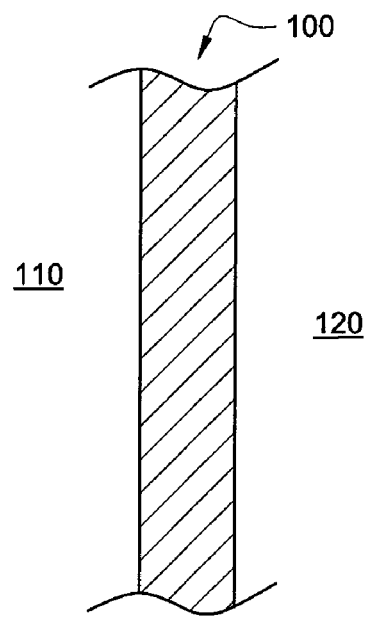
FIG. 1 illustrates an embodiment of a selectively permeable barrier employed for conversion of conjugated olefins to Diels-Alder adduct via a Diels-Alder reaction.

Unless otherwise noted, the figures may not be to scale.

DETAILED DESCRIPTION OF THE INVENTION

The process of the present invention comprises the use of a Diels-Alder type reaction to remove conjugated olefins from a monoolefin-containing fluid. The monoolefin-containing fluid may comprise a single monoolefin or may comprise a mixture of more than one monoolefin structure. The term "fluid" denotes gas, liquid, vapor, or combinations thereof. The Diels-Alder type reaction utilizes a Diels-Alder dienophile, preferably a Diels-Alder dienophile, to react with a conjugated diene (conjugated olefin) to form a Diels-Alder adduct. An example of the reaction is as follows:

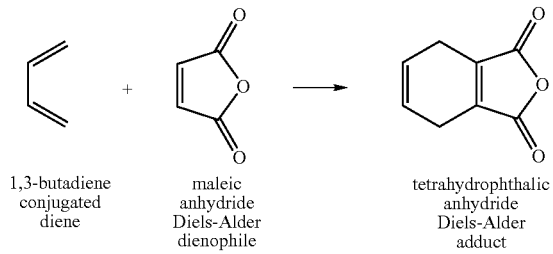

1,3-butadiene conjugated diene    maleic anhydride Diels-Alder dienophile    tetrahydrophthalic anhydride Diels-Alder adduct The term "Diels-Alder dienophile" refers to any Diels-Alder dienophile which can be used in the Diels-Alder reaction described herein. The term "Diels-Alder adduct" refers to any adduct which is provided according to the Diels-Alder reaction described herein.

Examples of suitable dieneophiles include, but are not limited to ethylenes, acetylenes, cyclics, and the like and combinations thereof. Examples of suitable ethylenes include, but are not limited to, ethylenes having a general structure $R^1R^2C=CR^3R^4$ where $R^1$=H, C(=O)OR$^5$, C(=O)R$^6$, C(=O)NR$^7R^8$, CN, $C_1$ to $C_{30}$ alkyl, and aromatic,
$R^2$=H, C(=O)OR$^5$, C(=O)R$^6$, C(=O)NR$^7R^8$, CN, $C_1$ to $C_{30}$ alkyl, and aromatic,
$R^3$=H, C(=O)OR$^5$, C(=O)R$^6$, C(=O)NR$^7R^8$, CN, $C_1$ to $C_{30}$ alkyl, and aromatic,
$R^4$=H, C(=O)OR$^5$, C(=O)R$^6$, C(=O)NR$^7R^8$, CN, $C_1$ to $C_{30}$ alkyl, and aromatic,
$R^5$=$C_1$ to $C_{10}$ alkyl, aromatic, and (H)C=CH$_2$
$R^6$=$C_1$ to $C_{10}$ alkyl, aromatic, and (H)C=CH$_2$
$R^7$=$C_1$ to $C_{10}$ alkyl, aromatic, and
$R^8$=$C_1$ to $C_{10}$ alkyl, aromatic.

Examples of suitable ethylenes include, but are not limited to, methyl acrylate, ethyl acrylate, methyl methacrylate, ethyl methacrylate, vinyl acrylate, dimethyl fumarate, dimethyl maleate, diethyl fumarate, diethyl maleate, diphenyl fumarate, divinyl fumarate, divinylmaleate, acrolein, methyl vinyl ketone, divinylketone, acrylamide, N,N-dimethyl acrylamide, N,N-dimethyl methacrylamide, N,N-diethyl acrylamide, N,N-diethyl acrylamide, acrylonitrile, methacrylonitrile, 1,1-dicyanoethylene, maleonitrile, fumaronitrile, tetracyanoethylene, and the like and combinations thereof.

Examples of suitable acetylenes include, but are not limited to, acetylenes having a general structure $R^1C=CR^2$ where $R^1$=H, C(=O)OR$^3$, C(=O)R$^4$, C(=O)NR$^5R^6$, CN, $C_1$ to $C_{10}$ alkyl, and aromatic,
$R^2$=H, C(=O)OR$^3$, C(=O)R$^4$, C(=O)NR$^5R^6$, CN, $C_1$ to $C_{10}$ alkyl, and aromatic,
$R^3$=$C_1$ to $C_{10}$ alkyl, and aromatic,
$R^4$=H, $C_1$ to $C_{10}$ alkyl, and aromatic,
$R^5$=$C_1$ to $C_{10}$ alkyl, and aromatic, and
$R^6$=$C_1$ to $C_{10}$ alkyl, and aromatic.

Examples of suitable acetylenes include, but are not limited to acetylene (ethyne), propyne, 1-butyne, 2-butyne, dimethyl acetylenedicarboxylate, diethyl acetylenedicaboxylate, phenyl acetylene, diphenyl acetylene, and the like and combinations thereof.

Examples of suitable cyclics include, but are not limited to, maleic derivations having a general structure

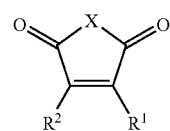

where X=O, N, and S,
$R^1$=H, $C_1$ to $C_{10}$ alkyl, and aromatic, and
$R^2$=H, $C^1$ to $C_{10}$ alkyl, and aromatic.

Additional examples of suitable cyclics include, but are not limited to, benzoquinone derivatives having a general structure

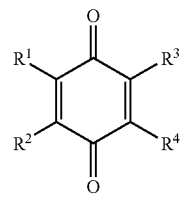

where $R^1$=H, $C_1$ to $C_{10}$ alkyl, aromatic, and (H)C=CH$_2$,
$R^2$=H, $C_1$ to $C_{10}$ alkyl, aromatic, and (H)C=CH$_2$,
$R^3$=H, $C_1$ to $C_{10}$ alkyl, aromatic, and (H)C=CH$_2$, and
$R^4$=H, $C_1$ to $C_{10}$ alkyl, aromatic, and (H)C=CH$_2$.

Examples of suitable maleic derivatives include, but are not limited to, maleic anhydride, methyl maleic anhydride, dimethyl maleic anhydride, maleimide, N-methyl maleimide, N-ethyl maleimide, methyl maleimide, dimethyl maleimide, methyl-N-methyl maleimide, dimethyl-N-methyl maleimide, and the like and combinations thereof.

Examples of suitable benzoquinone derivatives include 1,4-benzoquinone, 2-methylbenzoquinone, 2,3-dimethylbenzoquinone, 2,5-dimethylbenzoquinone, 2,6-dimethylbenzoquinone, 2,3,5-trimethylbenzoquinone, 2,3,5,6-tetramethylbenzoquinone, and the like and combinations thereof.

Preferred Diels-Alder dienophiles useful in a process of the present invention include, but are not limited to, maleic anhydride, derivatives of maleic anhydride, benzoquinone, derivatives of benzoquinone, dialkyl fumarates, dialkyl maleates, dialkylacetylenedicarboxylates, and the like and combinations thereof. More preferred Diels-Alder dienophiles useful in a process of the present invention include maleic anhydride, dimethyl acetylene dicarboxylate, benzoquinone, and combinations thereof. The most preferred dienophlie useful in a process of the present invention is maleic anhydride.

The term conjugated olefin used throughout this specification refers any olefin having at least one pair of double bonds in conjugation. The conjugated olefin may have additional double bonds that may or may not be conjugated. The simplest example of a conjugated olefin is 1,3 butadiene. Examples of suitable conjugated olefins include, but are not limited to, conjugated olefins generally comprising at least about four carbon atoms per molecule and no more than about ten carbon atoms per molecule, preferably comprising at least about four carbon atoms per molecule and no more than about eight carbon atoms per molecule, and more preferably comprising at least about four carbon atoms per molecule and no more than about six carbon atoms per molecule.

Examples of suitable conjugated olefins containing four carbon atoms per molecule include 1-3 butadiene. Examples of suitable conjugated olefins containing five carbon atoms per molecule include 1,3-pentadiene and 2-methyl-1,3-butadiene, preferably 1,3-pentadiene.

Examples of suitable conjugated olefins containing six carbon atoms per molecule include, but are not limited to, 1,3-hexadiene, 2,4-hexadiene, 1,3,5-hexatriene, 2-methyl-1,3-pentadiene, 2,3-dimethyl-1,3-butadiene and 3-methyl-1,3-pentadiene. Preferred conjugated olefins containing six carbon atoms per molecule include 1,3-hexadiene, 2,4-hexadiene, 1,3,5-hexatriene, and the like and combinations thereof. More preferred conjugated olefins containing six carbon atoms per molecule include 1,3-hexadiene.

Examples of suitable conjugated olefins containing seven carbon atoms per molecule include, but are not limited to, 1,3-heptadiene, 2,4-heptadiene, 1,3,5-heptatriene, and the like and combinations thereof. Preferred conjugated olefins containing seven carbon atoms per molecule include 1,3-heptadiene.

Examples of suitable conjugated olefins containing eight carbon atoms per molecule include, but are not limited to, 1,3-octadiene, 2,4-octadiene, 3,5-octadiene, 1,3,5-octatriene, 2,4,6-octatriene, 1,3,5,7-octatetraene, and the like and combinations thereof. Preferred conjugated olefins containing eight carbon atoms per molecule include 1,3-octadiene.

Examples of suitable conjugated olefins containing nine carbon atoms per molecule include, but are not limited to, 1,3-nonadiene, 2,4-nonadiene, 3,5-nonadiene, 1,3,5-nonatriene, 2,4,6-nonatriene, 1,3,5,7-nonatetraene, and the like and combinations thereof. Preferred conjugated olefins containing nine carbon atoms per molecule include 1,3-nonadiene.

Examples of suitable conjugated olefins containing ten carbon atoms per molecule include but are not limited to, 1,3-decadiene, 2,4-decadiene, 3,5-decadiene, 4,6-decadiene, 1,3,5-decatriene, 2,4,6-decatriene, 3,5,7-decatriene, 1,3,5,7-decatetraene, 2,4,6,8-decatetraene, 1,3,5,7,9-decapentaene, and the like and combinations thereof. Preferred conjugated olefins containing ten carbon atoms per molecule include 1,3-decadiene.

The adduct, preferably Diels-Alder adduct, can be separated from the monoolefin-containing fluid by any separating means known in the art capable of separating an adduct from a monoolefin-containing fluid. Examples of suitable separating means include, but are not limited to, distillation, adsorption, membrane separation, and the like, and combinations thereof. The Diels-Alder adduct typically has a substantially higher molecular weight than the monoolefin-containing fluid being purified. Thus, conventional distillation is generally capable of separating the Diels-Alder adduct. Another way to accomplish the separation is by performing the conjugated diene/Diels-Alder dienophile reaction and Diels-Alder adduct separation or removal in a reactive distillation apparatus. For example, the boiling point of 1-butene is −6.3° C. and the boiling point of tetrahydrophthalic anhydride is greater than 100° C. For reference, the boiling point of butadiene is −4.5° C.

Examples of suitable monoolefins for use in a process of the present invention include, but are not limited to, normal alpha olefins. Examples of suitable normal alpha olefins include, but are not limited to, 1-butene, 1-pentene, 1-hexene, 1-heptene, 1-octene, 1-nonene, 1-decene, and the like and combinations thereof. Preferred normal alpha olefins include 1-butene, 1-pentene, 1-hexene, and combinations thereof.

The conjugated olefins and monoolefins in a fluid comprising such conjugated olefins and monoolefins to be used in a process of the present invention preferably contain the same number of carbon atoms. For example, a preferred fluid for use in a process of the present invention comprises a monoolefin of 1-butene and a conjugated diolefin of 1,3-butadiene.

In an embodiment, the concentration of conjugated olefins (e.g. dienes) in a treated composition is reduced by converting the conjugated olefins to a Diels-Alder adduct and arresting the Diels-Alder adduct. In an embodiment, a composition comprising mono-olefins and conjugated olefins is treated via contact thereof with a Diels-Alder dienophile to convert conjugated olefins to a Diels-Alder adduct, wherein the Diels-Alder dienophile and Diels-Alder adduct are arrested during such contact. In an embodiment, arresting is such that the Diels-Alder dienophile and Diels-Alder adduct do not mix homogeneously with a bulk of the composition before, during, and/or after treatment. In another embodiment, arresting is such that within a given volume having two parts relative to one another, there exists a first part having a high concentration of Diels-Alder dienophile and Diels-Alder adduct and a second part having a low concentration of Diels-Alder dienophile and Diels-Alder adduct. In an embodiment, the bulk of the composition is the part having a low concentration of Diels-Alder dienophile and Diels-Alder adduct.

In an embodiment, the Diels-Alder adduct is arrested about simultaneously with the formation thereof. In an embodiment, the Diels-Alder adduct is arrested about concurrently with the formation thereof. In an embodiment, the Diels-Alder adduct is arrested about instantaneously with the formation thereof. In an embodiment, the Diels-Alder adduct is arrested about immediately following the formation thereof. In an embodiment, the Diels-Alder adduct is arrested in situ with the formation thereof.

In an embodiment, the contacting and the arresting occur about simultaneously. In an embodiment, the contacting and arresting occur about concurrently. In an embodiment, the contacting and arresting occur about instantaneously. In an embodiment, the arresting occurs about immediately after the contacting. In an embodiment, the contacting and arresting occur in situ. In an embodiment, the contacting and arresting occur in a common or shared processing step. In an embodiment, the contacting and arresting occur in a common or shared receptacle or vessel.

In an embodiment, a composition comprising conjugated olefins is fed to a contact zone and a composition having a reduced amount of conjugated olefins is recovered from the contact zone, wherein the conjugated olefins are contacted with a Diels-Alder dienophile to from a Diels-Alder adduct within the contact zone and the Diels-Alder dienophile and Diels-Alder adduct are arrested within the contact zone. In an embodiment, the contact zone is disposed within a larger reaction zone such as a vessel, reactor, container, tank, etc. In an embodiment, the contact zone is a partition of the larger zone. In an embodiment, the contact zone, reaction zone, or both may be optionally agitated or mixed to facilitate contact, including the embodiments set forth in FIGS. 1 to 6. In an embodiment, the part having a low concentration of Diels-Alder dienophile and Diels-Alder adduct is optionally agitated or mixed.

In an embodiment, arresting is such that the Diels-Alder dienophile and Diels-Alder adduct are confined within a defined volume. In an embodiment, the Diels-Alder dienophile and Diels-Alder adduct are confined by a selectively permeable barrier such as a membrane that is permeable to mono-olefins and conjugated olefins and non-permeable to Diels-Alder dienophile and Diels-Alder adduct. In an embodiment, the defined volume is the part having a higher concentration of Diels-Alder dienophile and Diels-Alder adduct than the bulk of the composition. In an embodiment, the defined volume is the contact zone.

In an embodiment, the arresting is such that the Diels-Alder dienophile, Diels-Alder adduct, or both are confined within a phase that is different from a phase comprising the composition, that is the arresting is carried out via a phase differential. In an embodiment, a phase comprising the Diels-Alder dienophile and Diels-Alder adduct defines the contact zone. In an embodiment, a phase comprising the composition is the part having a lower concentration of Diels-Alder dienophile and Diels-Alder adduct than the contact zone. In embodiments, a phase comprising the Diels-Alder dienophile and Diels-Alder adduct may be a solid, a liquid, a gas, or combinations thereof and the phase comprising the composition may be a liquid, a gas, or combinations thereof, wherein the two phases do not comprise a same phase. The contacting conditions and or the identity of the composition, Diels-Alder dienophile, and Diels-Alder adduct may determine the phase thereof. In an embodiment, the phase comprising the Diels-Alder dienophile and Diels-Alder adduct is a liquid and the phase comprising the composition is a gas. In an embodiment, the phase comprising the Diels-Alder dienophile and Diels-Alder adduct is a solid and the phase comprising the composition is a liquid, a gas, or both.

Arresting the Diels-Alder dienophile and Diels-Alder adduct from the composition may eliminate the need for further processing to separate the Diels-Alder dienophile and Diels-Alder adduct from the composition after contacting. In an embodiment, after contacting and arresting the resulting Diels-Alder adduct, the treated composition comprises a concentration of conjugated olefins of less than or equal to about 80 parts per million (ppm) by weight; alternatively, less than or equal to about 50 ppm; alternatively, less than or equal to about 25 ppm; alternatively, less than or equal to about 10 ppm; alternatively, less than or equal to about 1 ppm. In an embodiment, the treated composition comprises a concentration of Diels-Alder adduct of less than or equal to about 5 weight percent; alternatively, less than or equal to about 1 weight percent; alternatively, less than or equal to about 0.5 weight percent; alternatively, less than or equal to about 0.25 weight percent; alternatively, less than or equal to about 0.1 weight percent; alternatively, less than or equal to about 0.01 weight percent; alternatively, less than or equal to about 0.001 weight percent. In an embodiment, the treated composition comprises a concentration of Diels-Alder dienophile in the composition of less than or equal to about 5 weight percent; alternatively, less than or equal to about 1 weight percent; alternatively, less than or equal to about 0.5 weight percent; alternatively, less than or equal to about 0.25 weight percent; alternatively, less than or equal to about 0.1 weight percent; alternatively, less than or equal to about 0.01 weight percent; alternatively, less than or equal to about 0.001 weight percent. In an embodiment, the treated composition comprises a concentration of conjugated olefins that is 25% lower than the concentration in the untreated composition; alternatively, 50% lower than the concentration in the untreated composition; alternatively, 75% lower than the concentration in the untreated composition; alternatively, 90% lower than the concentration in the untreated composition; alternatively, 95% lower than the concentration in the untreated composition.

The temperature at which contacting occurs may be controlled. In an embodiment, contacting occurs at a temperature of greater than or equal to about 0° C. and less than or equal to about 150° C.; alternatively, at a temperature of greater than or equal to about 0° C. and less than or equal to about 120° C.; alternatively, at a temperature of greater than or equal to about 25° C. and less than or equal to about 90° C.; alternatively, at a temperature of greater than or equal to about 45° C. and less than or equal to about 60° C.

In addition to the temperature, the pressure at which contacting occurs may be controlled. In an embodiment, contacting occurs at a pressure of less than about 1500 psia; alternatively, at a pressure of less than atmospheric pressure; alternatively, at a pressure greater than or equal to about 1 psia and less than or equal to about 1500 psia; alternatively, at a pressure greater than or equal to about 1 psia and less than or equal to about 1000 psia; alternatively, less than about 1000 psia; alternatively, less than about 500 psia; alternatively, less than about 250 psia; alternatively, less than about 100 psia.

Figure 2A:
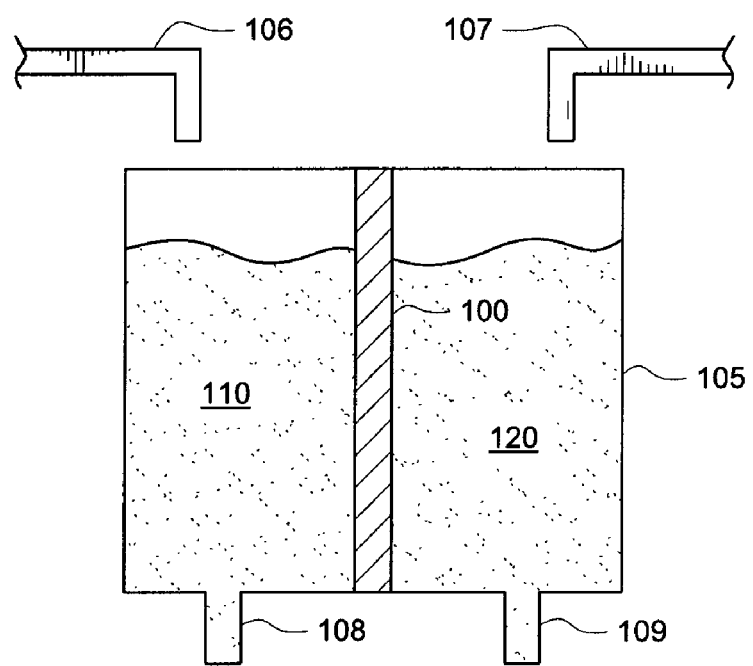
FIGS. 2A and 2B illustrate embodiments of a container comprising a selectively permeable barrier employed for conversion of conjugated olefins to Diels-Alder adduct via a Diels-Alder reaction.
Figure 2B:
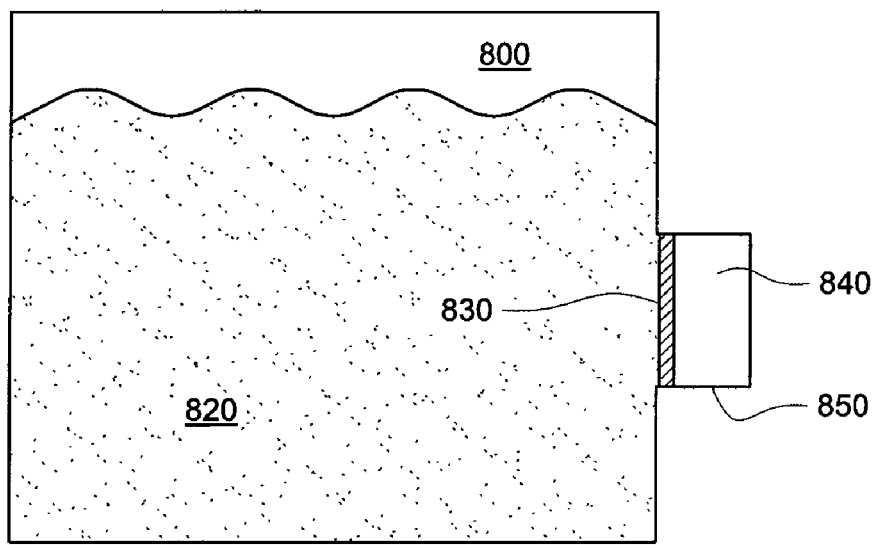

In an embodiment illustrated by FIG. 1, a Diels-Alder dienophile is confined to a first side 110 of a selectively permeable barrier such as a membrane 100. A composition comprising mono-olefins and conjugated olefins may be contacted with the second side 120 of the membrane 100, such that the mono-olefins and conjugated olefins may permeate the membrane 100 and contact the Diels-Alder dienophile. As conjugated olefins contact the Diels-Alder dienophile, Diels-Alder adduct is formed. As the membrane 100 is less permeable to Diels-Alder dienophile and Diels-Alder adduct, the Diels-Alder adduct is confined to the first side 110 of the membrane 100 along with the Diels-Alder dienophile. Thus, conjugated olefins in the composition on the second side 120 of the membrane are removed from the composition as they are converted to Diels-Alder adduct that is confined on the first side 110 of the membrane 100. The conversion of conjugated olefins and confinement of Diels-Alder adduct reduces the concentration of conjugated olefins in the composition on the second side 120 of the membrane 100. The membrane 100 may be placed in any suitable physical configuration or structure to form the first side 110 and second side 120. For example as shown in FIG. 2A, the membrane 100 may be disposed in a tank or vessel 105 having inlets 106 and 107 and outlets 108 and 109 for adding and removing components from first side 110 and second side 120, respectively. As shown in FIG. 2B, the membrane 830 may be disposed in a takeoff or partition 850 in vessel 800 to form first side 840 and second side 820. In an alternative embodiment not shown, the takeoff 850 is located on the bottom of vessel 800, thereby allowing the composition to permeate membrane 830 and travel downward by gravity for recovery of a composition having a reduced concentration of conjugated olefins and arresting the Diels-Alder dienophile and Diels-Alder adduct in vessel 800.

The permeability of appropriate selectively permeable barriers such as membranes may vary for different components, such as conjugated olefins, mono-olefins, Diels-Alder adduct, and Diels-Alder dienophile. In an embodiment, the selectively permeable barrier (e.g., membrane) is selected such that the composition has a higher permeation across the barrier than the Diels-Alder dienophile, the Diels-Alder adduct, or both. In an embodiment, the selectively permeable membrane is substantially impermeable to the Diels-Alder dienophile, the Diels-Alder adduct, or both. In an embodiment the selectively permeable barrier is selected such that the composition premeates the barrier more readily than the Diels-Alder dienophile and Diels-Alder adduct. In an embodiment, the Diels-Alder dienophile and Diels-Alder adduct permeate through the selectively permeable barrier at a rate that is less than 75% of the composition; alternatively, less than 50% of the composition; alternatively, less than 25% of the composition; alternatively, less than 10% of the composition; alternatively, less than 5% of the composition; alternatively, less than 1% of the composition. In an embodiment, the selectively permeable barrier is a membrane comprising an organic polymer. In an embodiment, the selectively permeable barrier is a membrane comprising an inorganic material. In an embodiment, the selectively permeable barrier is a membrane comprising alumina.

Figure 3:
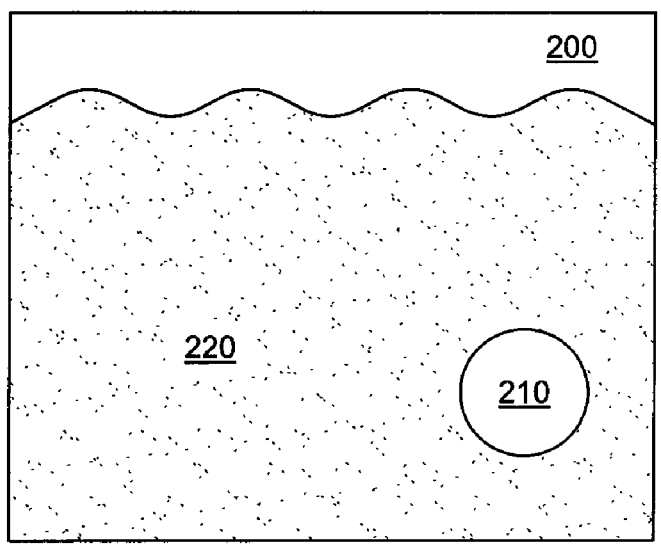
FIG. 3 illustrates an embodiment of a container comprising a selectively permeable barrier employed for conversion of conjugated olefins to Diels-Alder adduct via a Diels-Alder reaction.

FIG. 3 illustrates an embodiment employing a selectively permeable barrier (e.g., membrane). A container 210 comprising a selectively permeable barrier and containing a Diels-Alder dienophile may be placed in a vessel 200. The vessel 200 contains a composition 220 comprising mono-olefins and conjugated olefins. As discussed herein, the composition 220 comprising conjugated olefins may permeate the container 210 where contacting between conjugated olefins and the Diels-Alder dienophile forms a Diels-Alder adduct. The barrier confines the Diels-Alder adduct, thus reducing the concentration of-conjugated olefins in the composition. In an embodiment, vessel 200 is a transportation vessel or storage tank and container 210 is removable, pre-packaged, and sized to be placed in and treat the vessel and subsequently removed. In an embodiment, container is a flexible container such as a sack or bag formed from a membrane. In an embodiment, the container is reusable, for example by replacing Diels-Alder adduct with Diels-Alder dienophile. In an embodiment, the container is disposable.

Figure 4:
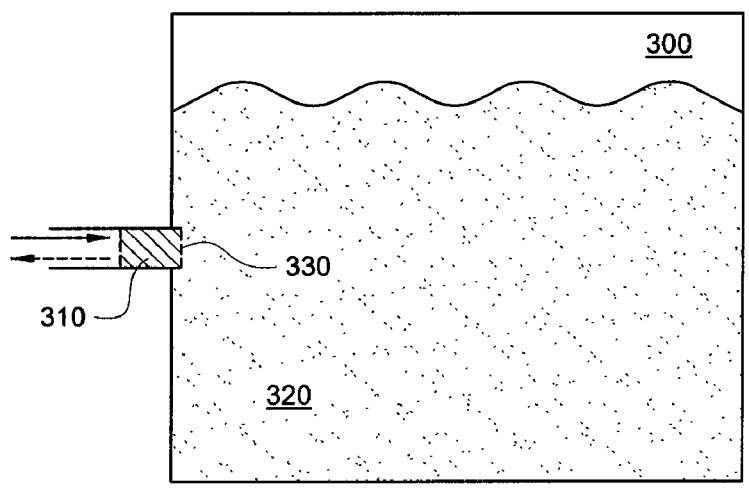
FIG. 4 illustrates an embodiment of a filter comprising a selectively permeable barrier employed for conversion of conjugated olefins to Diels-Alder adduct via a Diels-Alder reaction.

FIG. 4 illustrates an embodiment employing a selectively permeable barrier (e.g., membrane) that confines a Diels-Alder dienophile. A filter 310 comprising a selectively permeable barrier 330 and confining a Diels-Alder dienophile may be attached to a vessel 300 containing a composition 320. The filter 310 may be attached, for example, at an inlet or outlet of the vessel 300, or within a recirculation loop of the vessel 300. In embodiments, the Diels-Alder dienophile is a solid, liquid, or combinations thereof. The composition 320 comprising mono-olefins and conjugated olefins permeates the barrier 330 such that conjugated olefins may contact the Diels-Alder dienophile in the filter 310 to form a Diels-Alder adduct. In embodiments, the Diels-Alder adduct is a solid, liquid, or combinations thereof. The barrier 330 confines the Diels-Alder adduct, as well as the Diels-Alder dienophile, to the filter 310, thus reducing the concentration of conjugated olefins in the composition 320.

Figure 5:
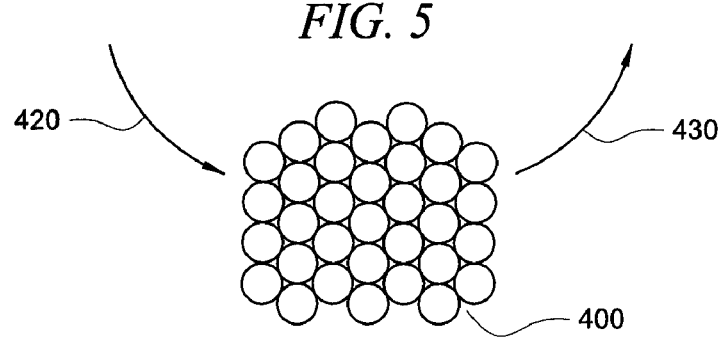
FIG. 5 illustrates an embodiment of a method for forming Diels-Alder adduct from conjugated olefins and arresting the Diels-Alder adduct from a composition in the same step.

FIG. 5 illustrates an embodiment for removing conjugated olefins from a composition comprising mono-olefins and conjugated olefins where removal occurs via a phase differential. Under the contacting conditions, the composition 420 may comprise fluids such as gases, liquids, or combinations thereof. The composition 420 is contacted with a Diels-Alder dienophile 400 that is a solid under the contacting conditions. Solid Diels-Alder dienophile may be coupled with an inert compound, e.g., alumina, activated carbon, or combinations thereof. Any of the Diels-Alder dienophiles disclosed herein that are solid under the desired processing conditions may be used. In an embodiment, the solid Diels-Alder dienophile comprises maleic anhydride, benzoquinone, or combinations thereof. The contacting converts conjugated olefins to a Diels-Alder adduct that is a solid under the contacting conditions. The phase differential arrests the Diels-Alder dienophile and Diels-Alder adduct from the fluid composition 420, such that the bulk composition after contacting 430 contains a lower concentration of conjugated olefins. The solid Diels-Alder adduct separates, e.g., precipitates, from the fluid composition as it is formed by the Diels-Alder reaction.

Figure 6:
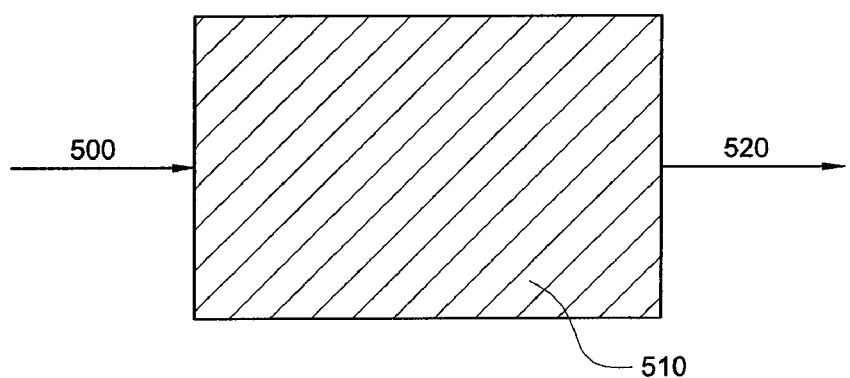
FIG. 6 illustrates an embodiment of a filter bed for converting conjugated olefins to Diels-Alder adduct via a Diels-Alder reaction and also arresting the Diels-Alder adduct in the filter bed.
Figure 7:
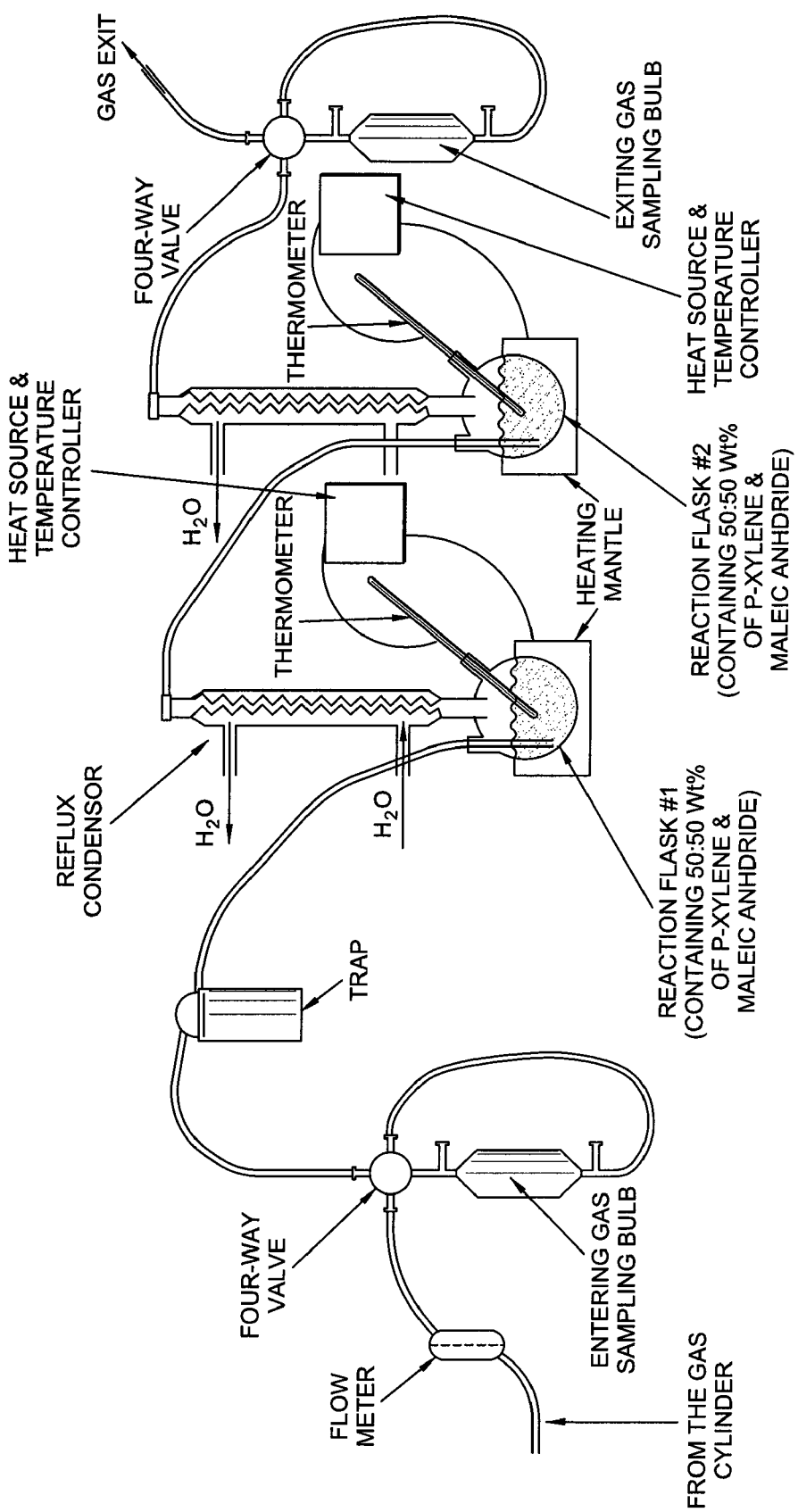
FIG. 7 is a schematic of the apparatus used for Examples 1 and 2.

FIG. 6 illustrates an embodiment for separating conjugated olefins from a composition comprising mono-olefins and conjugated olefins via employing a filter bed. In embodiments, the filter bed 510 comprises Diels-Alder dienophile that may be solids, liquids, gases, or combinations thereof. In an embodiment, the Diels-Alder dienophile is a solid. A composition comprising conjugated olefins and mono-olefins is fed to the filter bed 510. In embodiments, the composition in line 500 comprises olefins that are fluids such as gases, liquids, or combinations thereof. The conjugated olefins are contacted with the Diels-Alder dienophile in filter bed 510 to form a Diels-Alder adduct.

In an embodiment, the Diels-Alder dienophile in the filter bed 510 and Diels-Alder adduct are solids under the contacting conditions and the composition in line 500 is a fluid such as a gas, liquid, or both. Conversion of the fluid conjugated olefins to a solid Diels-Alder adduct separates the Diels-Alder adduct from the fluid composition in the filter bed 510 such that the output 520 from the filter bed 510 comprises a composition with a lower concentration of conjugated olefins. In an embodiment, the filter bed 510 comprises a compound that does not react with and/or absorb the composition, the Diels-Alder dienophile, the Diels-Alder adduct, or combinations thereof. In an embodiment, the filter bed comprises a compound that absorbs the Diels-Alder dienophile, the Diels-Alder adduct, both, which helps to reduce the amount thereof in the treated composition. In an embodiment, the filter bed comprises alumina, activated carbon, or combinations thereof. In an embodiment, the filter bed comprises alumina and is absorbent to the Diels-Alder dienophile, Diels-Alder adduct, or both.

EXAMPLES

The following examples, 1 and 2, are merely representative of aspects of the present invention and, as one skilled in the art would recognize, the present invention may be practiced without many of the aspects illustrated by the examples.

The following tests were performed in order to determine the effectiveness of a process of the present invention in removing conjugated olefins from a fluid comprising such conjugated olefins and monoolefins.

Examples 1 and 2

Apparatus

A 1-butene stream, containing 1,3-butadiene, was passed through two reaction vessels (three-necked round-bottomed flasks) containing a Diels-Alder dienophile solution. The reaction vessels were equipped with a reflux condenser, heating mantel, a thermometer, and a magnetic stirring apparatus. Both reaction vessels were assembled with the 1-butene inlet in the first neck, the reflux condenser mounted on the middle neck, and the thermometer affixed to the third neck. Butene flow control was achieved with a gas flow controller. Temperature control was achieved by connecting the thermometer and heating mantel to a temperature controlled electrical outlet. Feed and treated 1-butene samples were obtained through use of sampling bulbs which could be isolated from the reaction apparatus via use of 4-way valves. The 1-butene flow reaction apparatus elements, for Examples 1 and 2, were connected by Teflon® tubes. A schematic of the apparatus is represented in FIG. 7.

Example 1

Procedure

Two Diels-Alder dieneophile solutions of 75 grams of maleic anhydride, in 75 grams of p-xylene, were heated to 90° C. A 1-butene stream, containing 50 ppm 1,3-butadiene, was passed through the reaction vessels containing the Diels-Alder dienophile solution at a flow rate of 0.15 to 0.2 cubic ft/hour. The 1-butene stream and reactor effluent samples were obtained from the feed and exit gas sampling bulbs and analyzed by gas chromatography. The results are summarized in Table 1.

Example 2

Procedure

Example 2 was performed using the same procedure as Example 1 with the following exceptions: a recrystalized maleic anhydride sample was used and the starting 1,3 butadiene concentration was 72 ppm. The results are summarized in Table 1.

Examples 3 through 32

Apparatus

Figure 8:
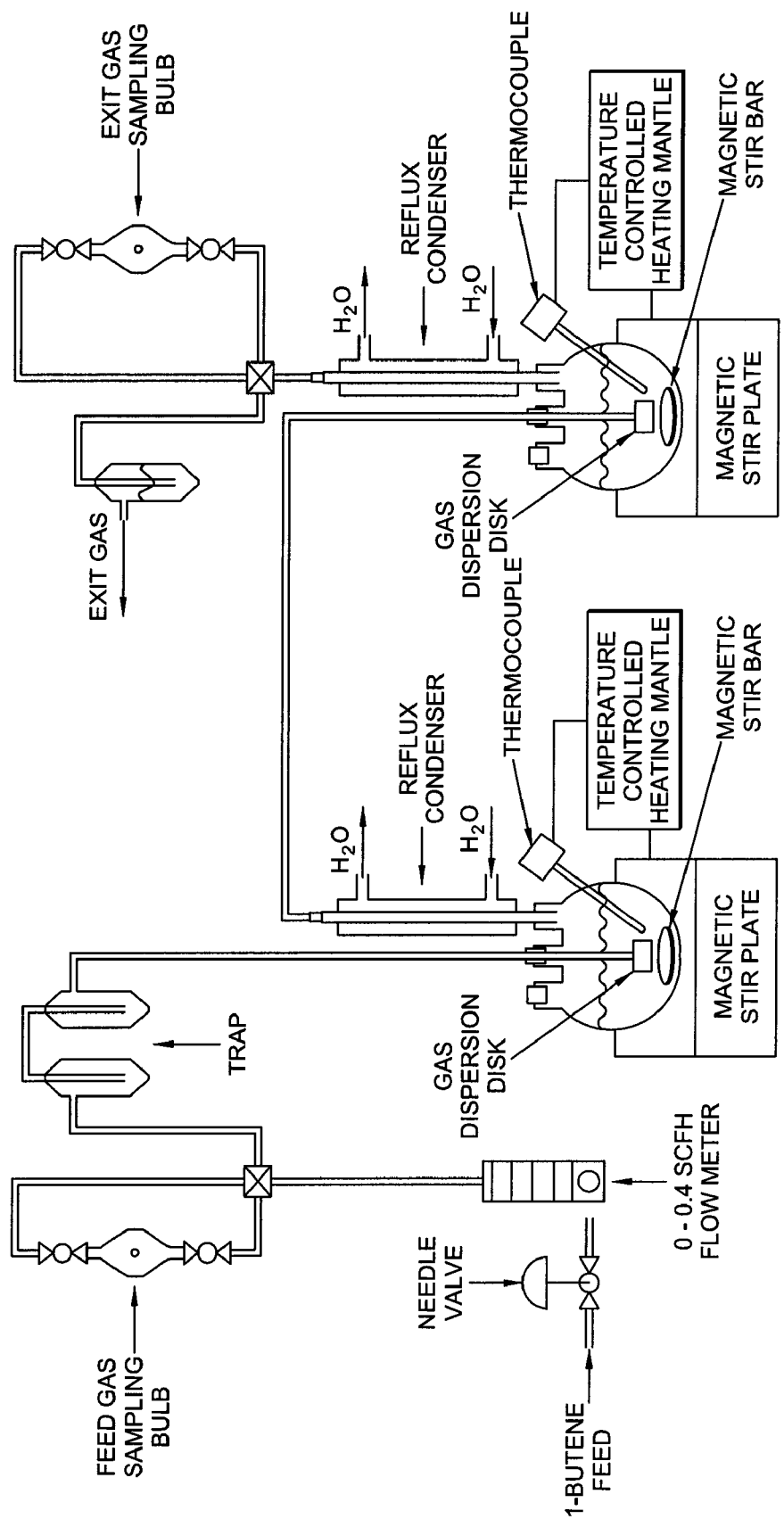
FIG. 8 is a schematic of the apparatus used for Examples 3 through 32.

A 1-butene stream, containing 1,3-butadiene, was passed, through gas dispersion tubes, through two reaction vessels (a three-necked round-bottomed flask) containing a Diels-Alder dienophile. The reaction vessels were equipped with a reflux condenser, heating mantel, a thermocouple, and a magnetic stirring apparatus. Both reaction vessels were assembled with the 1-butene inlet gas dispersion tube located in the center neck, the reflux condenser mounted on the third neck, and the thermometer affixed to the thermometer neck. The first neck was closed with a rubber septum. Butene flow control was achieved with a needle valve and a gas flow controller. Temperature control was achieved by connecting the thermocouple and heating mantel to a temperature controlled electrical outlet. Feed and treated 1-butene samples were obtained through use of sampling bulbs which could be isolated from the reaction apparatus via use of 4-way valves. The 1-butene flow reaction apparatus elements, for Examples 3 through 32, were connected by Teflon® tubes. A schematic of the apparatus is represented in FIG. 8.

Examples 3 through 32

Procedure

A 1-butene stream, containing approximately 67 to 72 ppm 1,3-butadiene, was passed through the reaction vessels containing the Diels-Alder dieneophile solutions, composed of a Diels-Alder dienophile in a solvent in amounts as recited in Table 1, at a flow rate of 0.2 or 0.4 cubic ft/hour at a temperature of between 60° C. and 148° C. The 1-butene stream and reactor effluent samples were obtained from the feed and exit gas sampling bulbs and analyzed by gas chromatography. The results are summarized in Table 1.

TABLE 1

Experimental examples for the removal of conjugated olefins from a monoolefin-containing fluid using a Diels-Alder dieneophile

| Example | Dienophile (amount) | Solvent (amount) | Temp. (° C.) | Flow Rate (cubic ft/hour) | Butadiene level of Exit Fluid (ppm) |
|---|---|---|---|---|---|
| 1 | Maleic Anhydride (75 g) | p-xylene (75 g) | 90 | 0.15-0.20 | 7.0 |
| 2 | Re-crystallized Maleic Anhydride (75 g) | p-xylene (75 g) | 90 | 0.15-0.20 | <1.0 |
| 3 | Maleic Anhydride (75 g) | o-xylene (90 mL) | 90 | 0.2 | 5.7 |
| 4 | Maleic Anhydride (75 g) | o-xylene (90 mL) | 90 | 0.4 | 8.8 |
| 5 | Maleic Anhydride (75 g) | o-xylene (90 mL) | 60 | 0.2 | 6.8 |
| 6 | Diethyl Fumarate (120 g) | o-xylene (120 mL) | 60 | 0.2 | 47.8 |
| 7 | Diethyl Fumarate (120 g) | o-xylene (120 mL) | 90 | 0.2 | 49.3 |
| 8 | Diethyl Fumarate (120 g) | o-xylene (120 mL) | 120 | 0.2 | 31.4 |
| 9 | Dimethyl Acetylene Dicarboxylate (100 mL) | o-xylene (100 mL) | 60 | 0.2 | 46.2 |
| 10 | Dimethyl Acetylene Dicarboxylate (100 mL) | o-xylene (100 mL) | 90 | 0.2 | 30.9 |
| 11 | Dimethyl Acetylene Dicarboxylate (100 mL) | o-xylene (100 mL) | 120 | 0.2 | 16.0 |
| 12 | Maleic Anhydride (75 g) | o-xylene (90 mL) | 90 | 0.2 | 6.4 |
| 13 | Maleic Anhydride (75 g) | o-xylene (90 mL) | 120 | 0.2 | 10.0 |
| 14 | Maleic Anhydride (75 g) | o-xylene (90 mL) | 120 | 0.4 | 14.5 |
| 15 | 1,4-Benzoquinone (100 g) | o-xylene (120 mL) | 90 | 0.2 | 11.7 |
| 16 | 1,4-Benzoquinone (100 g) | o-xylene (120 mL) | 90 | 0.4 | 19.9 |
| 17 | 1,4-Benzoquinone (100 g) | o-xylene (120 mL) | 120 | 0.2 | 12.4 |
| 18 | Phenylacetylene (100 mL) | o-xylene (100 mL) | 60 | 0.2 | 66.1 |
| 19 | Methyl Vinyl Ketone (100 mL) | o-xylene (100 mL) | 60 | 0.2 | 57.3 |
| 20 | Hexadecene (200 mL) | — | 90 | 0.2 | 68.0 |
| 21 | Hexadecene (200 mL) | — | 120 | 0.2 | 70.0 |
| 22 | Hexadecene (200 mL) | — | 148 | 0.2 | 69.8 |

TABLE 1-continued

Experimental examples for the removal of conjugated olefins
from a monoolefin-containing fluid using a Diels-Alder dieneophile

| Example | Dienophile (amount) | Solvent (amount) | Temp. (° C.) | Flow Rate (cubic ft/hour) | Butadiene level of Exit Fluid (ppm) |
|---|---|---|---|---|---|
| 23 | Methyl Vinyl Ketone (100 mL) | Hexadecane (100 mL) | 80 | 0.2 | 63.4 |
| 24 | Maleic Anhydride (100 g) | Hexadecane (100 mL) | 60 | 0.2 | 7.1 |
| 25 | Maleic Anhydride (100 g) | Hexadecane (100 mL) | 90 | 0.2 | 6.3 |
| 26 | Maleic Anhydride (100 g) | Hexadecane (100 mL) | 90 | 0.4 | 12.3 |
| 27 | Maleic Anhydride (100 g) | Hexadecane (100 mL) | 120 | 0.4 | 10.7 |
| 28 | Dimethyl Acetylene Dicarboxylate (100 mL) | Hexadecane (100 mL) | 60 | 0.2 | 44.1 |
| 29 | Dimethyl Acetylene Dicarboxylate (100 mL) | Hexadecane (100 mL) | 90 | 0.2 | 29.3 |
| 30 | Dimethyl Acetylene Dicarboxylate (100 mL) | Hexadecane (100 mL) | 90 | 0.4 | 31.9 |
| 31 | Ethyl Propiolate (100 mL) | Hexadecane (100 mL) | 60 | 0.2 | 58.8 |
| 32 | Ethyl Propiolate (100 mL) | Hexadecane (100 mL) | 90 | 0.2 | 64.0 |

The results shown in the above examples clearly demonstrate that the present invention is well adapted to carry out the objects and attain the ends and advantages mentioned as well as those inherent therein.

Reasonable variations, modifications, and adaptations can be made within the scope of the disclosure and the appended claims without departing from the scope of this invention.

Example 33

Figure 9:
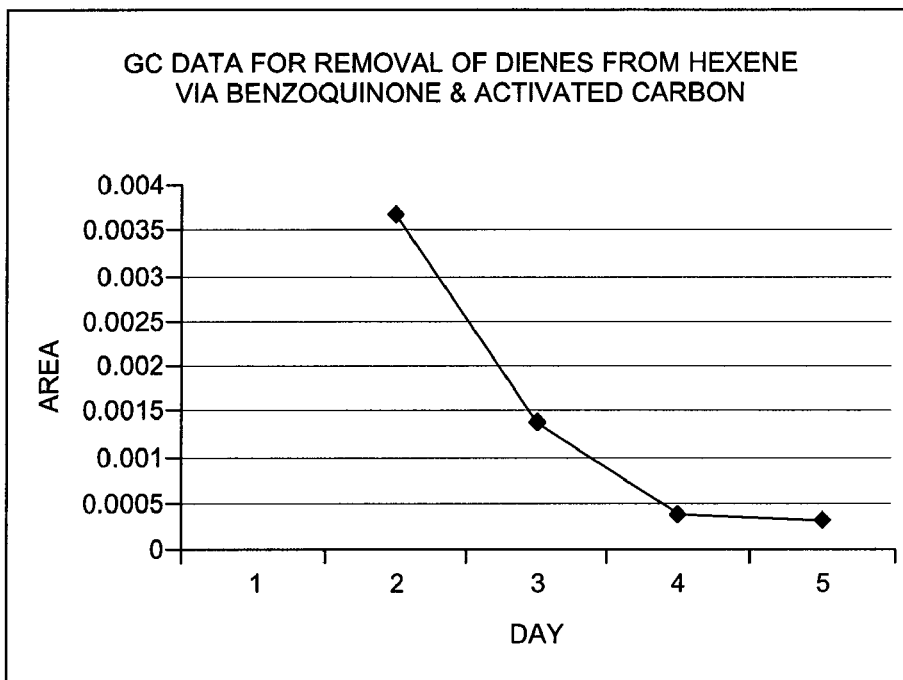
FIG. 9 is a chart illustrating the change in concentration of conjugated olefins (dienes) in a composition via a Diels-Alder reaction involving benzoquinone as provided herein.

A 250 milliliter chromatographic glass filtration column was loaded with the following items in the order in which they are listed: glass wool; about 10 grams of sand; about 10 grams of neutral alumina; about 8 grams of activated carbon; 2 grams of solid benzoquinone; about 8 grams of activated carbon; about 10 grams of neutral alumina; and about 10 grams of sand. The items were compacted by tapping the column after addition of each item. The column was then filled with hexene. The liquid was allowed to percolate through the layers of items and then the filtration column was plugged to prevent liquid from dripping. After an entire day, samples were taken once each day in a GC vial and run on an HP6890. The observed reduction in diene concentration is reflected by the GC data in Table 2, which is also charted in FIG. 9.

TABLE 2

| Date | Sample # | Ret Time | Area | PPM |
|---|---|---|---|---|
| Jul. 29, 2003 | Feed | 9.875 | 0.00368 | 37 |
| Jul. 30, 2003 | 1st | 9.974 | 0.00139 | 14 |
| Jul. 31, 2003 | 2nd | 9.962 | 0.0004 | 4 |
| Aug. 1, 2003 | 3rd | 9.963 | 0.00036 | 3.6 |

Example 34

Figure 10:
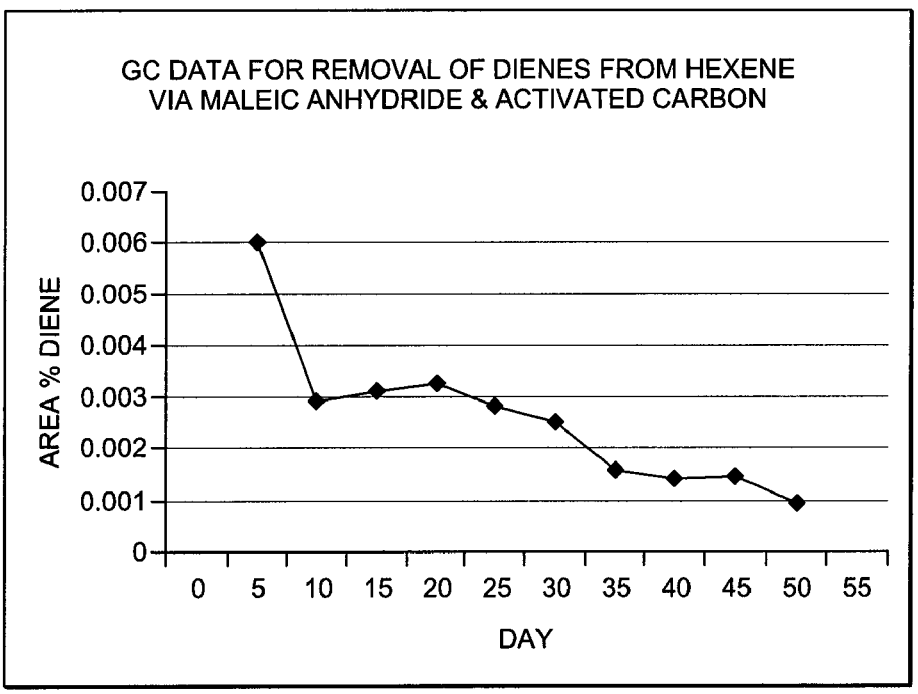
FIG. 10 is a chart illustrating the change in concentration of conjugated olefins (dienes) in a composition via a Diels-Alder reaction involving maleic ahydride as provided herein.

The equipment and procedure employed in Example 34 were identical to the equipment and procedure employed in Example 33, except that solid maleic anhydride replaced benzoquinone. The observed reduction in diene concentration is reflected by the GC data in Table 3, which is also charted in FIG. 10.

TABLE 3

| Date | Sample # | Ret Time | Area | PPM |
|---|---|---|---|---|
| Jun. 3, 2003 | Hexene | 9.887 | 0.00606 | 60.6 |
| Jun. 4, 2003 | 1st | 9.897 | 0.00295 | 29.5 |
| Jun. 5, 2003 | 2nd | 9.902 | 0.00315 | 31.5 |
| Jun. 9, 2003 | 3rd | 9.886 | 0.0033 | 33 |
| Jun. 11, 2003 | 4th | 9.885 | 0.00287 | 28.7 |
| Jun. 16, 2003 | 5th | 9.904 | 0.00257 | 25.7 |
| Jun. 17, 2003 | 6th | 9.888 | 0.00166 | 16.6 |
| Jun. 23, 2003 | 7th | 9.89 | 0.00149 | 14.9 |
| Jun. 24, 2003 | 8th | 9.879 | 0.00152 | 15.2 |
| Jul. 1, 2003 | 9th | 9.88 | 0.00101 | 10.1 |

While the present invention has been illustrated and described above in terms of particular apparatus and methods of use, it is apparent that, having the benefit of the teachings herein, equivalent techniques and ingredients may be substituted for those shown, and other changes can be made within the scope of the present invention as defined by the appended claims.

What is claimed as our invention is:

1. A method for removing conjugated olefins from a composition comprising:
    contacting the composition with a Diels-Alder dienophile to convert conjugated olefins to a Diels-Alder adduct; and
    arresting the Diels-Alder adduct via a selectively permeable barrier or a phase differential.

2. The method of claim 1 further comprising arresting the Diels-Alder dienophile.

3. The method of claim 1 wherein the selectively permeable barrier is a membrane.

4. The method of claim 1 wherein the Diels-Alder adduct is a solid and the composition is not a solid.

5. The method of claim 4 wherein the Diels-Alder dienophile comprises maleic anhydride, benzoquinone, or combinations thereof.

6. The method of claim 1 wherein the Diels-Alder adduct is a liquid and the composition is not a liquid.

7. The method of claim 1 wherein the selectively permeable barrier is disposed in a vessel.

8. The method of claim 7 wherein the selectively permeable barrier forms a removable container arresting the Diels-Alder adduct.

9. The method of claim 4 wherein the solids are disposed in a filter.

10. The method of claim 9 wherein the filter comprises alumina, activated carbon, or combinations thereof.

11. The method of claim 1 further comprising recovering a composition having a lower concentration of conjugated olefins.

12. The method of claim 11 wherein the recovered composition comprises less than or equal to about 80 parts per million by weight of conjugated olefins.

13. The method of claim 11 wherein the lower concentration of conjugated olefins is about 25 percent lower.

14. The method of claim 11 wherein the recovered composition comprises less than or equal to about 5 weight percent of Diels-Alder dienophile.

15. The method of claim 11 wherein the recovered composition comprises less than or equal to about 5 weight percent of Diels-Alder adduct.

16. A method comprising:
confining a Diels-Alder dienophile to a first side of a selectively permeable barrier wherein the barrier is more permeable to conjugated olefins and less permeable to Diels-Alder dienophile and Diels-Alder adduct; and
contacting a composition comprising mono-olefins and conjugated olefins with the Diels-Alder dienophile to form Diels-Alder adduct;
wherein the contacting reduces the concentration of conjugated olefins in the composition.

17. The method of claim 16 wherein the contacting further comprises exposing the composition to a second side of the barrier such that conjugated olefins permeate to the first side of the barrier.

18. The method of claim 17 wherein the contacting results in a lower concentration of conjugated olefins in the composition on the second side of the barrier.

19. The method of claim 18 wherein the Diels-Alder dienophile and Diels-Alder adduct are confined to the first side of the barrier.

20. A method for removing conjugated olefins from a composition comprising:
bubbling the composition through a liquid comprising Diels-Alder dienophile to form a liquid comprising Diels-Alder adduct; and
arresting the Diels-Alder adduct via a selectively permeable barrier or a phase differential,
wherein the bubbling and the arresting occur in a substantially common zone.

21. A method for removing conjugated olefins from a nonsolid composition comprising contacting the composition with a solid comprising Diels-Alder dienophile to form a solid comprising Diels-Alder adduct.

22. The method of claim 1 wherein the Diels-Alder dienophile and the Diels-Alder adduct do not mix homogenously with a bulk of the composition before, during, or after the contacting.

23. The method of claim 1 wherein the Diels-Alder adduct is arrested about simultaneously, about concurrently, about instantaneously, or about immediately following the formation of the Diels-Alder adduct.

24. The method of claim 1 wherein the composition further comprises mono-olefins.

25. The method of claim 20 wherein the composition further comprises mono-olefins.

26. The method of claim 1 wherein the Diels-Alder dienophile is maleic anhydride, derivatives of maleic anhydride, benzoquinone, derivatives of benzoquinone, dialkyl fumarates, dialkyl maleates, dialkylacetylenedicarboxylates, or combinations thereof.

27. The method of claim 1 wherein the Diels-Alder dienophile is maleic anhydride, dimethyl acetylene dicarboxylate, benzoquinone, or combinations thereof.

28. The method of claim 16 wherein the Diels-Alder dienophile is maleic anhydride, derivatives of maleic anhydride, benzoquinone, derivatives of benzoquinone, dialkyl fumarates, dialkyl maleates, dialkylacetylenedicarboxylates, or combinations thereof.

29. The method of claim 16 wherein the Diels-Alder dienophile is maleic anhydride, dimethyl acetylene dicarboxylate, benzoquinone, or combinations thereof.

30. The method of claim 20 wherein the Diels-Alder dienophile is maleic anhydride, derivatives of maleic anhydride, benzoquinone, derivatives of benzoquinone, dialkyl flimarates, dialkyl maleates, dialkylacetylenedicarboxylates, or combinations thereof.

31. The method of claim 20 wherein the Diels-Alder dienophile is maleic anhydride, dimethyl acetylene dicarboxylate, benzoquinone, or combinations thereof.

32. The method of claim 21 wherein the Diels-Alder dienophile is maleic anhydride, derivatives of maleic anhydride, benzoquinone, derivatives of benzoquinone, dialkyl fumarates, dialkyl maleates, dialkylacetylenedicarboxylates, or combinations thereof.

33. The method of claim 21 wherein the Diels-Alder dienophile is maleic anhydride, dimethyl acetylene dicarboxylate, benzoquinone, or combinations thereof.

* * * * *